(12) United States Patent
Boyes et al.

(10) Patent No.: US 9,526,815 B2
(45) Date of Patent: Dec. 27, 2016

(54) COMPOSITE HYDROGEL-CLAY PARTICLES

(75) Inventors: Victoria L. Boyes, South Yorkshire (GB); Chris Sammon, South Yorkshire (GB); Christine Lemaitre, South Yorkshire (GB); Chris Breen, South Yorkshire (GB)

(73) Assignee: SHEFFIELD HALLAM UNIVERSITY, Sheffield (GB)

( * ) Notice: Subject to any disclaimer, the term of this patent is extended or adjusted under 35 U.S.C. 154(b) by 406 days.

(21) Appl. No.: 14/240,200

(22) PCT Filed: Aug. 21, 2012

(86) PCT No.: PCT/GB2012/052046
§ 371 (c)(1),
(2), (4) Date: Apr. 11, 2014

(87) PCT Pub. No.: WO2013/027051
PCT Pub. Date: Feb. 28, 2013

(65) Prior Publication Data
US 2014/0219973 A1    Aug. 7, 2014

(30) Foreign Application Priority Data

Aug. 23, 2011   (GB) .................... 1114446.6

(51) Int. Cl.
| | | |
|---|---|---|
| *A61L 31/16* | (2006.01) | |
| *A61L 31/12* | (2006.01) | |
| *A61L 27/52* | (2006.01) | |
| *A61L 31/14* | (2006.01) | |
| *C08K 3/34* | (2006.01) | |
| *A61L 27/24* | (2006.01) | |
| *A61L 27/38* | (2006.01) | |
| *A61L 27/44* | (2006.01) | |

(52) U.S. Cl.
CPC .............. *A61L 31/128* (2013.01); *A61L 27/24* (2013.01); *A61L 27/3808* (2013.01); *A61L 27/44* (2013.01); *A61L 27/52* (2013.01); *A61L 31/145* (2013.01); *A61L 31/16* (2013.01); *C08K 3/346* (2013.01); *A61L 2300/20* (2013.01)

(58) Field of Classification Search
None
See application file for complete search history.

(56) References Cited

U.S. PATENT DOCUMENTS

| | | | |
|---|---|---|---|
| 2003/0194491 A1 | 10/2003 | Gold et al. | |
| 2004/0220296 A1* | 11/2004 | Lowman ................ | A61F 2/441 523/113 |
| 2010/0239672 A1* | 9/2010 | Kemeny ................. | B82Y 30/00 424/487 |

FOREIGN PATENT DOCUMENTS

| | | | |
|---|---|---|---|
| EP | 1160286 A1 | 12/2001 | |
| JP | 2006095470 A | 4/2006 | |
| WO | WO2009041870 A1 | 4/2009 | |
| WO | WO 2011/051731 * | 5/2011 | ............. A61L 31/04 |

OTHER PUBLICATIONS

El-Herif et al., Polymer Bull., 2010, 66(6), pp. 721-734.*
Hazem et al., Polymer Bull., 2011, vol. 66, pp. 721-734.*
Lee et al., J. App. Poly. Sci., 2004, vol. 92, pp. 3422-3429.*
English language abstract and machine translation for JP2006095470 extracted from espacenet.com database, dated Jun. 19, 2014, 10 pages.
PCT International Search Report for PCT/GB2012/052046, dated Nov. 15, 2012, 3 pages.
Haraguchi, "Synthesis and Properties of Soft Nanocomposite Materials With Novel Organic/Inorganic Network Structures", Polymer Journal, vol. 43, No. 3, Mar. 2011, pp. 223-241.
Gong et al. "Double-Network Hydrogels with Extremely High Mechanical Strength", Advanced Materials, 2003, 15, No. 14, Jul. 17, 2003, pp. 1155-1158.
Haraguchi et al. "Nanocomposite Hydrogels: A Unique Organic-Inorganic Network Structure with Extraordinary Mechanical, Optical, and Swelling/De-swelling Properties", Advanced Materials, 14, No. 16, Aug. 16, 2002, pp. 1120-1124.
Hazem et al., "Superabsorbent Nanocomposite Hydrogels Based on Intercalation of Chitosan into Activated Bentonite", Polymer Bull. (2011) 66, pp. 721-734.
Huang et al. "A Novel Hydrogel with High Mechanical Strength: A Macromolecular Microsphere Composite Hydrogel", Advanced Materials, 19, 2007, pp. 1622-1626.
Lee et al., "Superabsorbent Polymeric Materials. XII. Effect of Montmorillonite on Water Absorbency for Poly(Sodium Acrylate) and Montmorillonite Nanocomposite Superabsorbents", Journal of Applied Polymer Science, (2004) vol. 92, pp. 3422-3429.
Okumura et al., "The Polyrotaxane Gel: A Topological Gel by Figure-of-Eight Cross-Links", Advanced Materials, 13, No. 7, Apr. 4, 2001.
Sakai et al. "Design and Fabrication of a High-Strength Hydrogel with Ideally Homogeneous Network Structure from Tetrahedron-Like Macromonomers", American Chemical Society, Macromolecules, (2008), 41, pp. 5379-5384.

* cited by examiner

*Primary Examiner* — Brian Gulledge
(74) *Attorney, Agent, or Firm* — Kirton McConkie; Evan R. Witt

(57) ABSTRACT

A nanocomposite hydrogel formed from free radical dissociation of an initiator and polymerization of a water soluble monomer. The resulting hydrogel finds particular application within the medical field for both soft and hard tissue repair in human and animals. The hydrogel is particularly advantageous for spinal disc repair.

23 Claims, 11 Drawing Sheets

COMPOSITE HYDROGEL-CLAY PARTICLES

RELATED APPLICATIONS

This application is the National Stage of International Patent Application No. PCT/GB2012/052046, filed on Aug. 21, 2012, which claims priority to and all the advantages of Great Britain Patent Application No. GB 1114446.6, filed on Aug. 23, 2011, the content of which is incorporated herein by reference.

The present invention relates to composite hydrogels and in particular, although not exclusively, to methods of preparation, precursor hydrogel formulations and methods of creating and/or implanting composite hydrogels in animals or humans.

Polymer hydrogels are formed as three dimensional polymer networks and contain large amounts of water and as such are soft, wet materials that are used in a wide variety of applications due to their physical characteristics. A specific category of hydrogels, termed 'chemically cross-linked polymer hydrogels' are particularly well suited for a number of practical applications such as soft contact lenses and superabsorbents, due largely to the network composition and ease of control of the extent of cross-linking and hence the degree of swelling in water and other solvents.

However, hydrogels that are chemically cross-linked have been found to have a number of limitations. This is due principally to a random arrangement of a large number of the chemical cross-links and a broad distribution of the linking chain lengths. Chemically cross-linked polymer hydrogels therefore exhibit (i) optical opacity at high cross-link density, (ii) poor mechanical strength and brittleness (independent of the cross-link density), and (iii) a low degree of swelling and a slow deswelling rate due to a restriction in the movement of the polymer chains.

A number of different approaches have been attempted to address the above problems resulting in the creation of new types of network structures. Example improvements include networks with sliding cross-links (slide-ring gels) [Okumura, Y. & Ito, K. *The polyrotaxane gel: a topological gel by figure-of-eight cross-links. Adv. Mater.* 13, 485-487 (2001)]; organic/inorganic networks (nanocomposite gels), [Haraguchi, K. & Takeshisa, T. *Nanocomposite hydrogels: a unique organic-inorganic network structure with extraordinary mechanical, optical, and swelling/de-swelling properties. Adv. Mater* 14, 1120-1124 (2002)]; interpenetrating networks (double-network gels) [Gong, J. P., Katsuyama, Y., Kurokawa, T. & Osada, Y. *Double-network hydrogels with extremely high mechanical strength. Adv. Mater.* 15, 1155-1158 (2003)]; self-assembled networks (macromolecular microsphere composite gels) [Huang, T., Hongguang, X., Jiao, K., Zhu, L., Brown, H. R. & Wang, H. *A novel hydrogel with high mechanical strength: a macromolecular microsphere composite hydrogel. Adv. Mater.* 19, 1622-1626 (2007)]; and networks with the same intercrosslink molecular weight (tetra-poly(ethylene glycol) (PEG) gels [Sakai, T., Matsunaga, T., Yamamoto, Y., Ito, C., Yoshida, R., Suzuki, S., Sasaki, N., Shibayama, M. & Chung, U., *I. Design and Fabrication of a high-strength hydrogel with ideally homogeneous network structure from tetrahedron-like macromonomers. Macromolecules* 41, 5379-5384 (2008)]. Of these approaches, nanocomposite gels formed from an organic polymer and an inorganic clay have proven to be most successful in trying to address the aforementioned problems associated with chemically cross-linked hydrogels. These clay based nanocomposites have been found to possess much improved mechanical optical, swelling and stimuli-sensitive properties.

During the course of their development, it was observed that the exfoliated inorganic clay within the nanocomposite gel acts as an effective multifunctional cross-linker in which the organic polymer chains are anchored onto the clay surface at one or both ends. The nanocomposite consists of long, flexible polymer chains connecting neighbouring clay sheets. It was proposed that the chain lengths between clay sheets may be proportional to the clay-clay inter-particle distance resulting in a relatively narrow distribution of chain lengths in contrast to the chemically cross-linked gels.

The established synthesis of nanocomposite gels involves free radical polymerisation of water soluble monomers containing amide groups. Suitable monomers include N-isopropylacrylamide (NIPAM), and N,N-dimethylacrylamide. Polymerisation occurs in situ in the presence of the inorganic clay that has been exfoliated and uniformly dispersed in an aqueous medium. A variety of clay minerals with layered and fibrous structures that disperse well in water have been used and examples include smectite-group clays (hectorite, saponite, montmorillonite and mica-group clays (synthetic fluorine mica) [Haraguchi, K. *synthesis properties of soft nanocomposite materials with novel organic/inorganic network structures. Polym. J.* 43, 223-241 (2011)].

JP 2006-95470; WO 2009/041870 and EP 1160286 disclose organic/inorganic hybrid hydrogel systems that incorporate clay-linked polymers.

However, there exists a need to develop further organic/inorganic nanocomposite gels to extend their utilisation to further applications.

Accordingly, the inventors provide a nanocomposite hydrogel and method of synthesis that find particular application within the medical field. In particular, the present hydrogel system allows a two stage synthesis involving the separation of the steps: free radical polymerisation and the final gelation. This is advantageous as the clay composite hydrogel can be maintained in a precursor suspension form, indefinitely prior to a desired time for hydrogel formation. According to one embodiment, this is achieved by selecting a thermally responsive initiator where disassociation occurs at a temperature appreciably above the gelation temperature of the resulting organic polymer-clay suspension.

Within the specification the term 'composite hydrogel precursor liquid' (CHPL) refers to the reaction mixture prior to free radical polymerisation of the monomer. Following free radical polymerisation, the term 'polymer-clay precursor hydrogel' (PCPH) is used to describe the fully reacted but not gelled suspension. This term therefore encompasses alternative terms to describe the precursor hydrogel such as polymer-clay composite hydrogel, composite hydrogel precursor, fully reacted composite hydrogel precursor, composite hydrogel precursor suspension, aqueous polymer-clay composite suspension, polymerised hydrogel liquid precursor, fully reacted or polymerised liquid gel.

Accordingly, one application for the present hydrogel system is the administration of the liquid phase PCPH, for example via injection, to an animal or human. The temperature of the PCPH may then be lowered and the resulting hydrogel formed in vivo at a desired location. Specific medical uses therefore include soft tissue, particularly spinal disc, or hard tissue repair.

Moreover, the majority of initiators and organic monomers that are suitable and used to form the hydrogels are toxic to living organisms thereby preventing doping of the hydrogels with biologically active species prior to polymerisation. The inventors have devised a system in which a biologically active species and other chemically sensitive compounds may be added to the PCPH (i.e. post polymerisation) but importantly prior to gelation. Accordingly, these biological species or dopant compounds are incorporated in situ within the resulting gelled structure. This is believed to be advantageous for controlled delivery/release of the active species in vivo as the composite structure is likely influenced by the presence of the active species during gelation.

Within this specification, reference to 'gelation' of the liquid phase PCPH, refers to the mechanism by which the liquid sets to form the gel. This mechanism is believed to involve one or both ends of all or a percentage of the polymer resultant from the polymerised water soluble monomer, anchoring or strongly attaching to the dispersed/exfoliated clay particles suspended in the aqueous medium. The resulting structure of the gel when the PCPH is lowered below the 'gelation' temperature is believed to comprise a plurality of polymer chains extending between the dispersed and exfoliated clay particles. As described previously, the clay particles in the present invention are considered to act as cross-linkages between the polymer chains in the gel matrix comprising interconnected clay and polymer species.

The viscosity of the PCPH is configured so as to be injectable through a needle or other small bore cannula to allow introduction of the suspension in to an animal or human body for subsequent gelation. Preferably, the suspension is suitable for injection through a 23 gauge needle or smaller. In particular, the viscosity of the present suspension is comparable to the viscosity of water.

According to a first aspect of the present invention there is provided a method of preparing a composite hydrogel comprising preparing an aqueous suspension containing (i) dispersed clay particles, (ii) a water soluble monomer and (iii) a radical initiator capable of free radical disassociation to form a composite precursor hydrogel liquid (CHPL); dissociating the radial initiator to provide free radical polymerisation of the monomer at a temperature above a gelation temperature of the resulting aqueous polymer-clay precursor hydrogel (PCPH); maintaining the PCPH in a fluid phase above the gelation temperature; reducing the temperature of the PCPH below its gelation temperature to provide a composite hydrogel.

Preferably, the water soluble monomer comprises an acrylamide. More preferably, the acrylamide monomer comprises a compound of formula I:

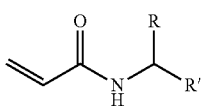

(I)

where R and R' are both alkyl, phenyl, alkyl-phenyl and preferably both R and R' are methyl groups.

Alternatively, the water soluble monomer is an acrylate compound of formula II:

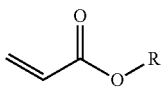

(II)

where R is a hydrophilic, acrylate or amide group.

Alternatively, the PCPH comprises any one or a combination of the following set of: a polymer formed from a single monomer; a polymer formed from at least two different monomers, a block copolymer.

Preferably, the monomer comprises any one or a combination of the following: acrylic acids; acid anhydrides; acrylates; sulfonic acids; vinyl sulfonates; pyrolidones; N-isopropylacrylamide (NIPAM); N,N-dimethylacrylamide, glycerol monomethacrylate, hydroxyl ethylmethacrylate, polyethyleneglycomethacrylate, vinyl pyrolidone; styrene sulphonic acid.

According to certain specific implementations, the gelation temperature of the PCPH is in the range 30° C. to 40° C. Additionally, the method further comprises heating the suspension containing the clay, the monomer and radical initiator to a temperature above the thermal dissociation temperature of the initiator to provide free radical dissociation of the initiator and subsequent polymerisation of the water soluble monomer. Preferably, the CHPL is heated to a temperature above 40° C. and optionally a temperature in the range 40° C. to 100° C. More preferably, this temperature is in the range 60° to 90° and more preferably 75° to 85°.

Advantageously, the clay particles, water soluble monomer and radical initiator and resulting polymerised suspension are not washed, cleaned or purified in any way and no recrystallisation of reagents and initiators is required. Additionally, there is no requirement to degas the reactants prior to use.

Preferably, the initiator comprises azobisisobutyronitrile (AIBN), 2,2'-azobis(2-methylpropionamide) (AIBA) or cyanovaleric acid (CVA).

Preferably, the clay particles are exfoliated in the aqueous suspension. More preferably, the clay comprises a swellable clay, capable of ion exchange. Even more preferably, the clay comprises any one or a combination of the following set of: montmorillonite; hectorite; saponite; vermiculite; mica; bentonite or a fibrous clay. The clay particles are highly dispersed within the composite suspension and preferably this dispersion is exfoliated or is approaching exfoliation. Optionally, the clay comprises: an organic cation exchanged clay; or an inorganic cation exchanged clay. Reference to 'clay particles' within this specification includes: individual clay layers or platelets, 'small groupings' of clay platelets and similar associations of fibrous clay particles. This term may also be considered to include layered double hydroxides incorporating a trivalent and a divalent metal such as Mg—Al hydroxides. As will be appreciated by those skilled in the art, these hydroxides have very similar appropriate characteristics to clay and may be regarded as alternatives to clay and clay particles within the scope of the present invention.

In particular, it is preferred that an aspect ratio of the non-fibrous clay particles is between 50 to 1000, where the aspect ratio is the relationship between the diameter and thickness of the nanoclay particles.

Preferably, the initial aqueous suspension comprises 7-10% NIPAM, 0.5 to 1.5% clay and an appropriate amount of radical initiator sufficient to fully polymerise the NIPAM with the remainder made up of water. Additional additives may then be added following polymerisation of the monomer.

Preferably, the method further comprises introducing into the PCPH at least one or a combination of biologically active species selected from the list of: mammalian cells such as stem cells; an antimicrobial; an antibody; a bacteria; a protein; a pharmaceutical; a peptide.

Optionally, the method may further comprise introducing into either the CHPL and/or the PCPH, a natural, non-synthetic compound or synthetic compound comprising any one or a combination of the following set: a water soluble polymer; hyaluronic acid; hydrophilic gels; polyethylene glycol, polypropylene glycol and mixtures thereof; cellulose ethers; chitosan; alginates; proteoglycans; natural starches; collagen; gelatine; hydroxyapatite.

Optionally, the method may further comprise introducing into the CHPL and/or the PCPH any one or a combination of the following process additives: a thickener; a rheology modifier; a surfactant; a pigment or dye; a radio opaque material.

According to a second aspect of the present invention there is provided a composite hydrogel precursor liquid (CHPL) comprising: water; a clay dispersed and suspended within the water at an amount not more than 5% by weight of the CHPL; a water soluble monomer at an amount not more than 25% by weight of the CHPL; a radical initiator capable of free radical polymerisation of the monomer; wherein the radical initiator comprises a thermal dissociation temperature that is above a gelation temperature of a resulting suspension containing a polymer-clay precursor hydrogel (PCPH) produced by the reaction with the radical initiator.

Optionally, the clay is not more than 2% by weight of the CHPL and the amount of the water soluble monomer is not more than 20% by weight of the CHPL.

According to a third aspect of the present invention there is provided a fluid phase polymer-clay precursor hydrogel (PCPH) suspension comprising: water; a clay dispersed and suspended within the water; a polymer resultant from the dissociation of a radial initiator to provide free radical polymerisation of a monomer in the presence of the clay at a temperature above a gelation temperature of the resulting PCPH suspension.

Optionally, the PCPH comprises a viscosity in the range 0.6 to 10 mPa·s at 54° C. Preferably, the PCPH comprises a viscosity in the range 0.6 to 5.0 mPa·s at 54° C. More preferably, the PCPH comprises a viscosity in the range 0.6 to 2.0 mPa·s at 54° C. Preferably, the PCPH comprises a density in the range 1000 to 1100 $Kg/m^3$ at 54° C. and in particular 1060 $Kg/m^3$ at 54° C.

The radical initiator is thermally stable and does not undergo free radical dissociation unless heated to and above its dissociation temperature. According to the subject invention, the initiator is selected such that the dissociation temperature is higher than the 'gelation' temperature of the polymer-clay precursor hydrogel (PCPH). Preferably the respective dissociation and gelation temperatures are separated by a difference in temperature in the range to 20° C. to 100° C.; 20° C. to 60° C. and more preferably around 40° C.

According to a fourth aspect of the present invention there is provided a composite hydrogel obtainable by a process of: preparing an aqueous suspension containing (i) dispersed clay particles, (ii) a water soluble monomer and (iii) a radical initiator capable of free radical disassociation to form a composite hydrogel precursor liquid (CHPL); dissociating the radial initiator to provide free radical polymerisation of the monomer at a temperature above a gelation temperature of a resulting aqueous polymer-clay precursor hydrogel (PCPH); maintaining the PCPH in a fluid phase above the gelation temperature; and reducing the temperature of the PCPH below its gelation temperature to provide the composite hydrogel.

According to a fifth aspect of the present invention there is provided a composite hydrogel obtainable from the PCPH as described herein by a process of: maintaining the PCPH in a fluid phase above the gelation temperature; and reducing the temperature of the PCPH below its gelation temperature to provide the composite hydrogel.

According to a sixth aspect of the present invention there is provided a method of creating a composite hydrogel in an animal or human in vivo comprising: injecting into a human or animal an aqueous polymer-clay precursor hydrogel (PCPH), the PCPH maintained above its gelation temperature before and during the step of injecting; allowing the temperature of the PCPH to decrease below the gelation temperature in vivo to form a composite hydrogel.

Preferably, the method comprises injecting the aqueous PCPH into a spinal disc of the animal or human. Optionally, the method may comprise injecting the aqueous PCPH into a region of soft or hard tissue of the animal or human. Optionally, the method may further comprise doping the aqueous PCPH with a biologically active species prior to the step of injecting.

The present hydrogel system is also suitable for wound dressing and is capable of exhibiting switchable absorption and donation characteristics so as to absorb or release desired compounds in response to a stimulus including for example, temperature, chemical or physical mechanical effects.

The present composite hydrogel is also suitable for non-medical use in particular, the specific uses of the composite hydrogel in both the low viscous liquid phase or the resulting gel state may include: textile coatings to provide a responsive breathable and porous coating for enhanced comfort and temperature regulation; filtration membranes to provide tailored absorption or switchable pore size driven or responsive to the membrane environment. The present gel may therefore act as a responsive selective filter of organic, inorganic and biological species; 'passive' windows where the gel is capable of switching between transparent and opaque states in response to raising and lowering the temperature. The present gels may therefore be coated or incorporated within existing glass and polymer window assemblies to reflect light and/or heat away from the building interior.

The present composite hydrogel may also be formed as a free-standing gel sheet or film. This may be achieved by coating or 'spreading' the PCPH on to a suitable release substrate using conventional coating heads. The present system may also be used to coat paper, textiles, films, glass or other substrates involving 'spreading' the liquid phase polymerised suspension onto the solid substrate followed by cooling.

The present system and in particular the polymer-clay composite suspension may be processed prior to and/or during the step of reducing the temperature of the suspension by casting, moulding, spinning, foaming, coating or spraying the suspension. Preferably, spinning comprises electro-spinning and fibre spinning.

Specific examples of the present invention will now be described referring to the accompanying drawings in which.

Figure 4:
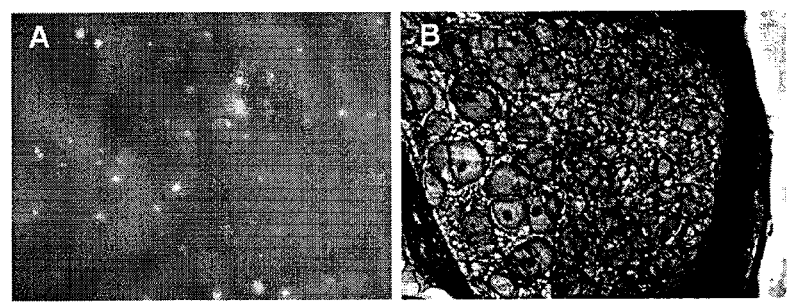
Figure 5:
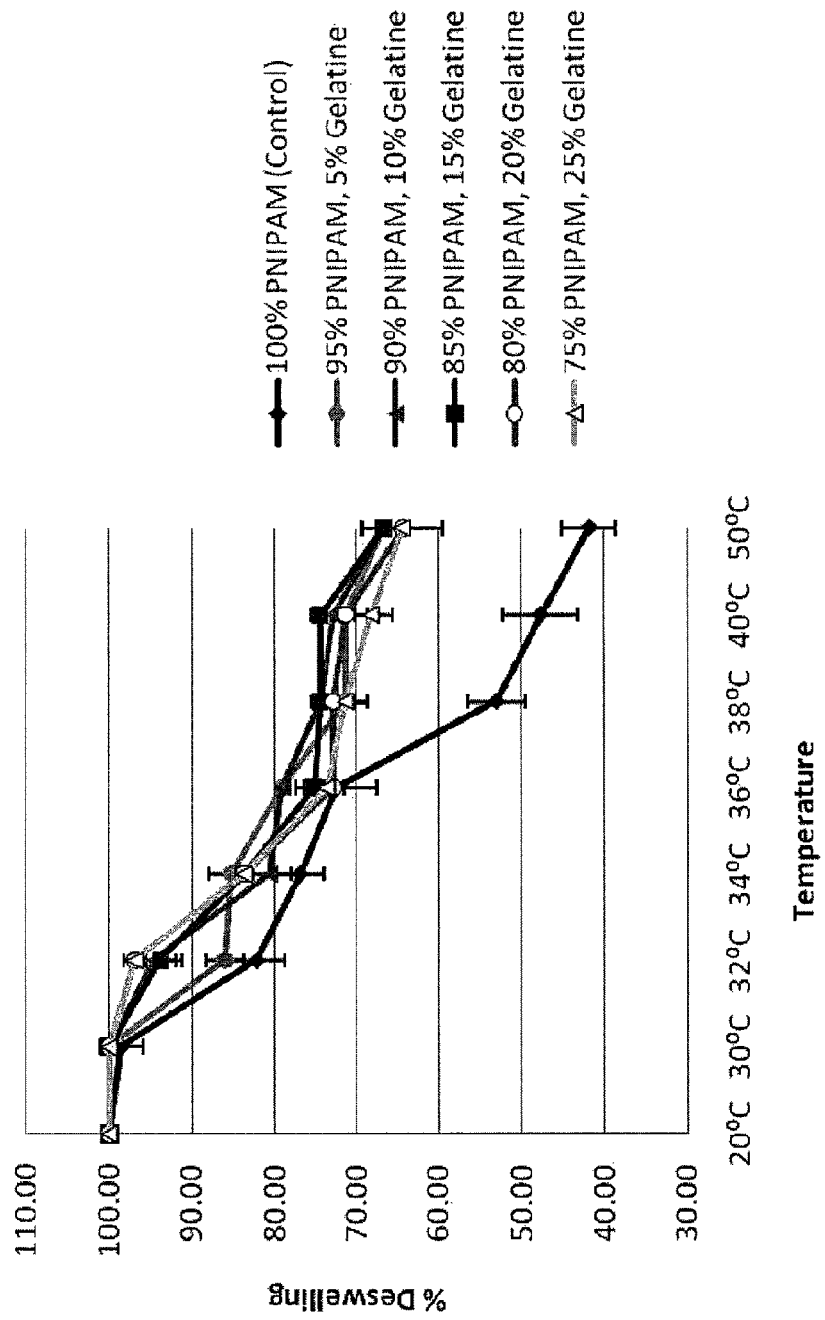
Figure 6:
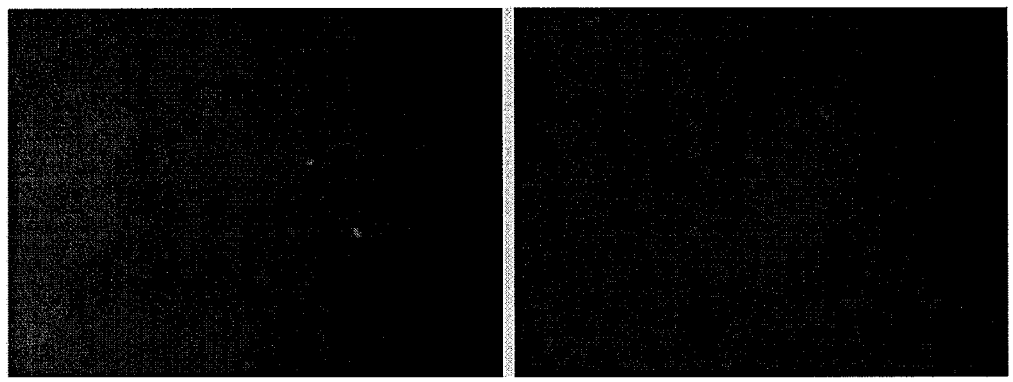
Figure 7:
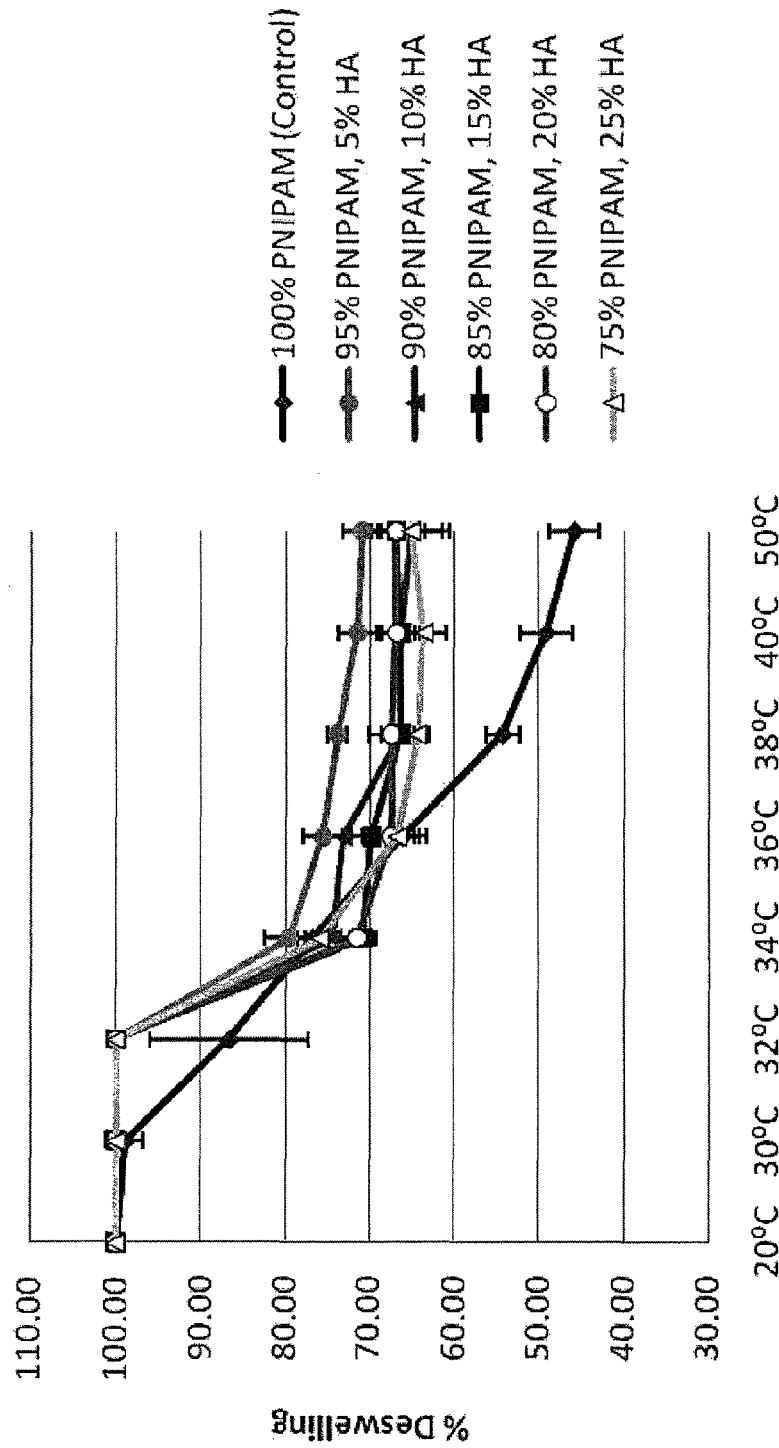
Figure 8:
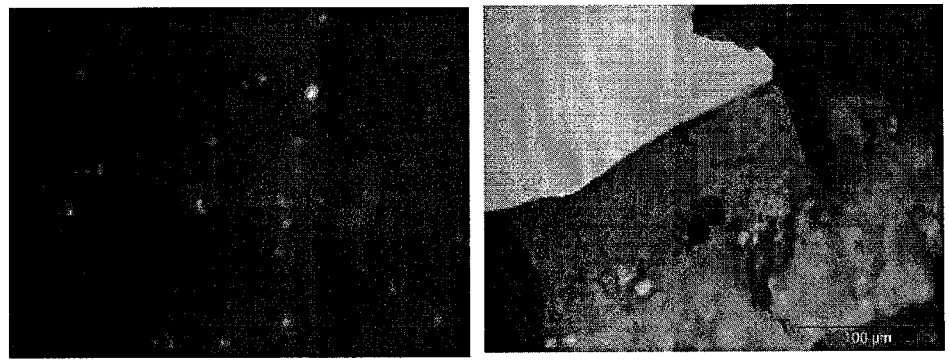
Figure 9:
Figure 10:
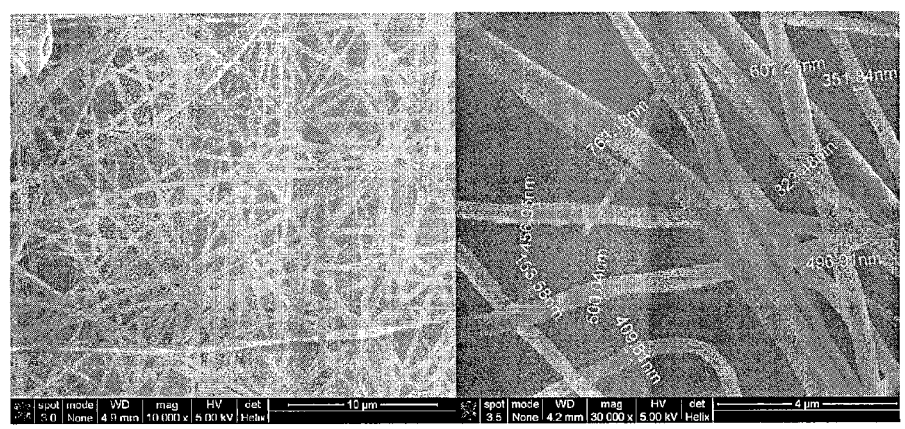
Figure 11:
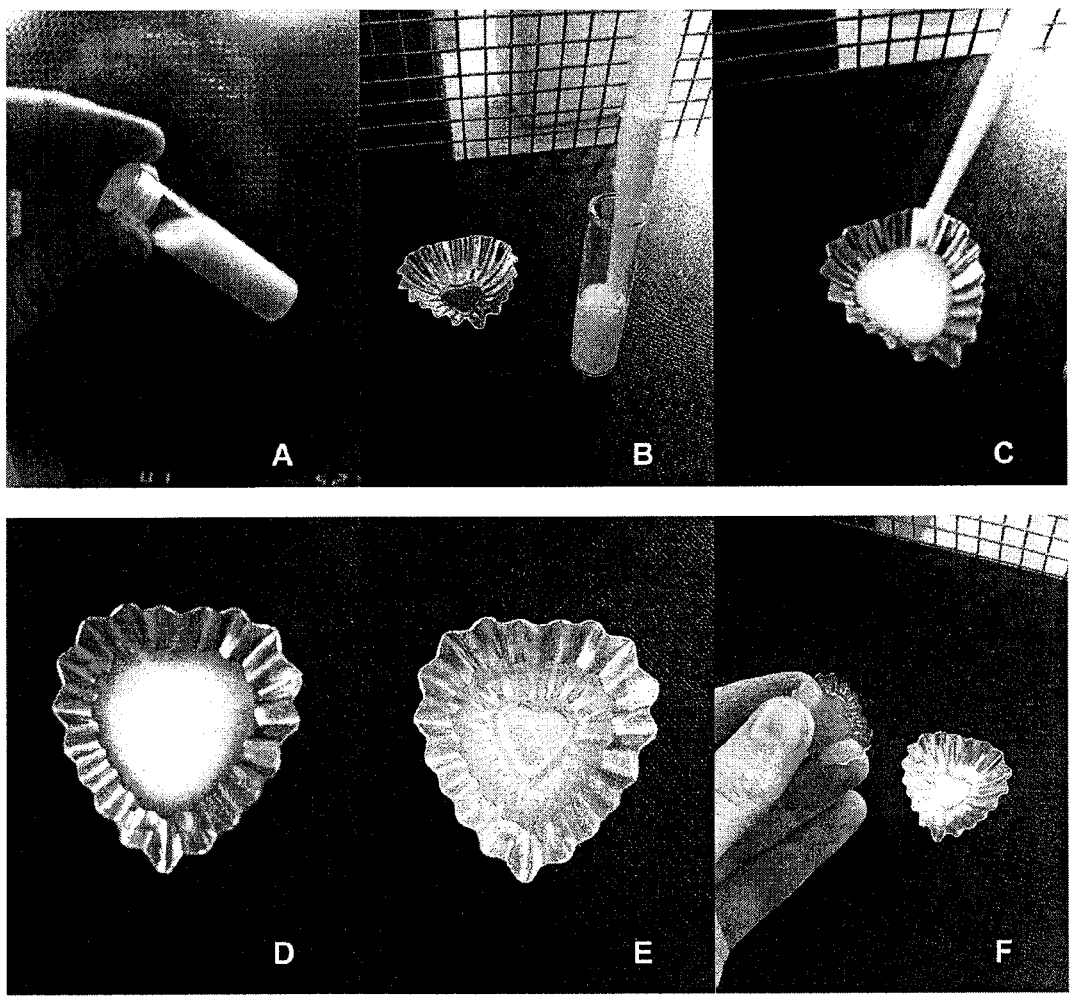
Figure 12:
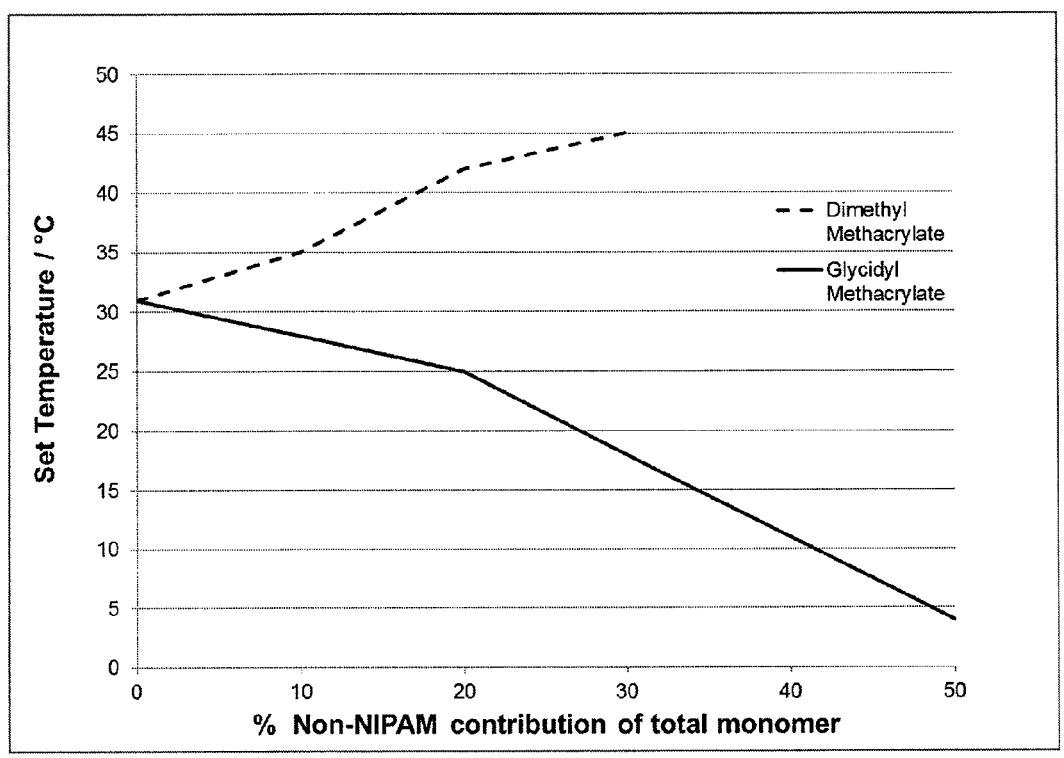
Figure 13:
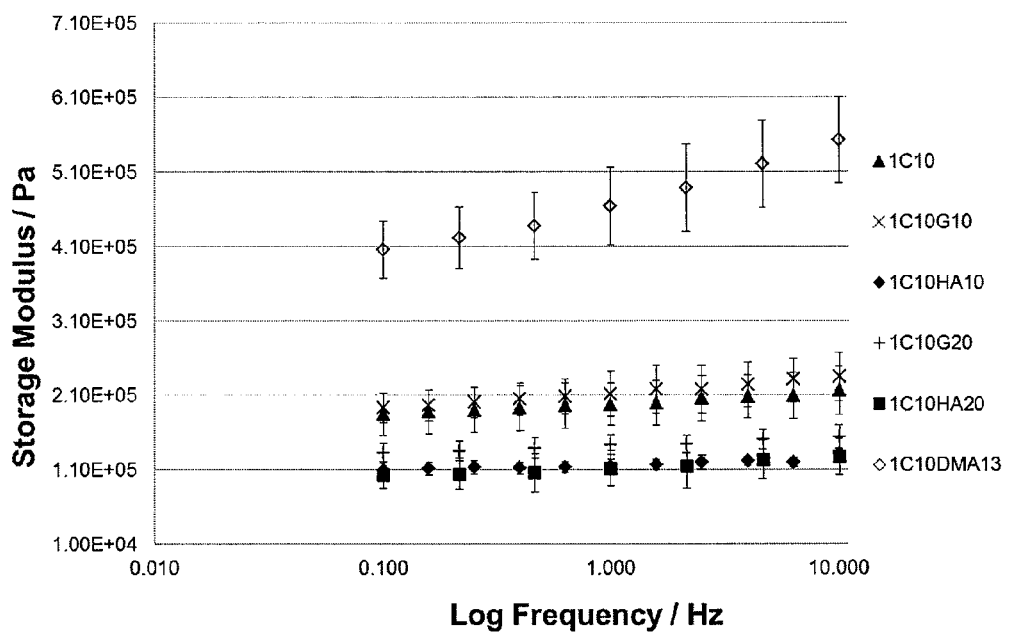
Figure 14:
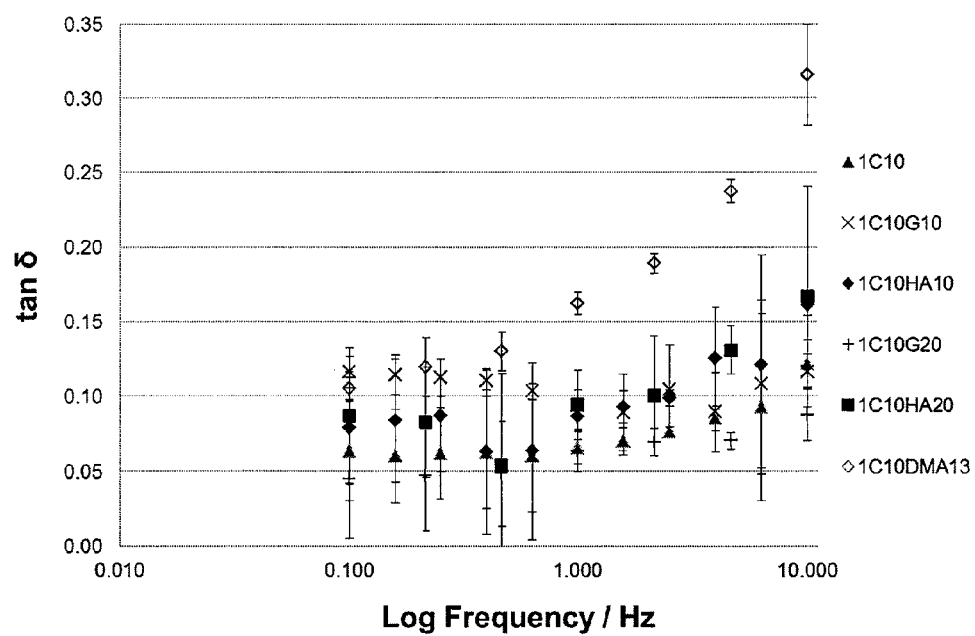
Figure 15:
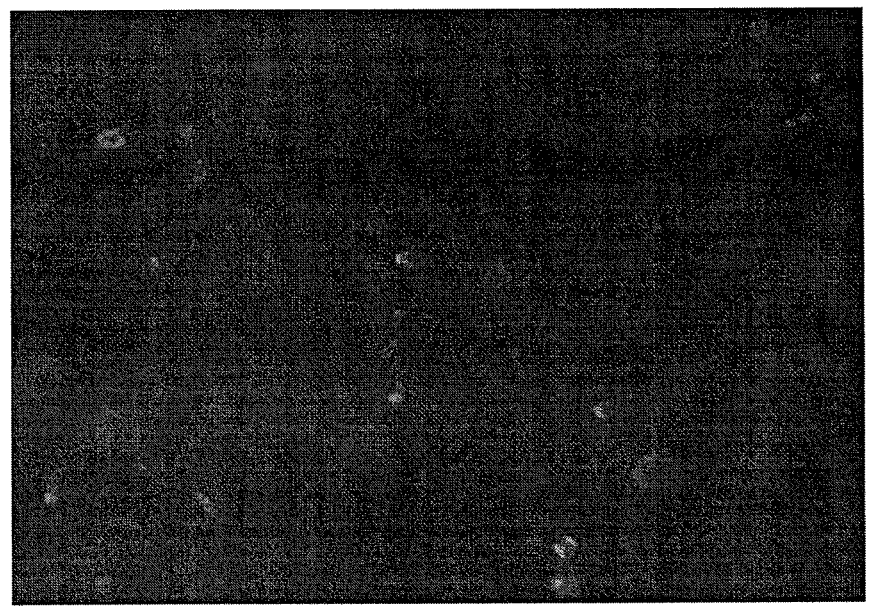
Figure 16:
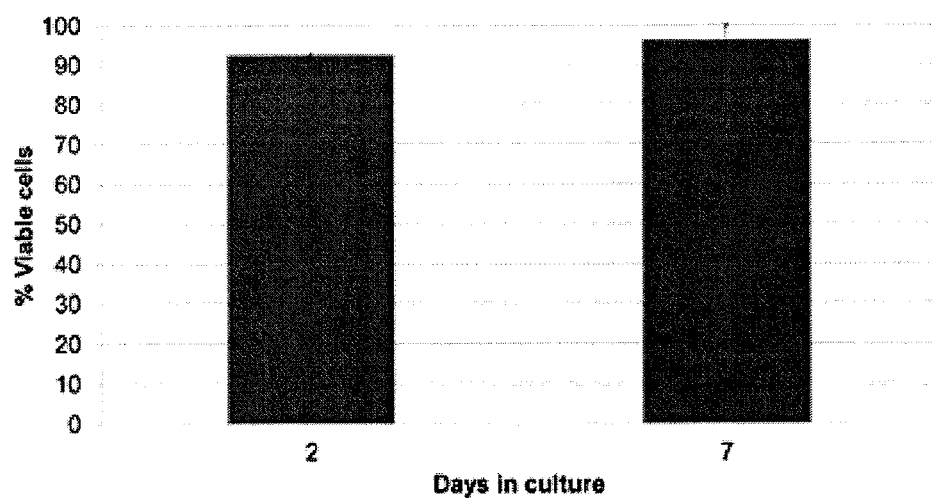
Figure 17:
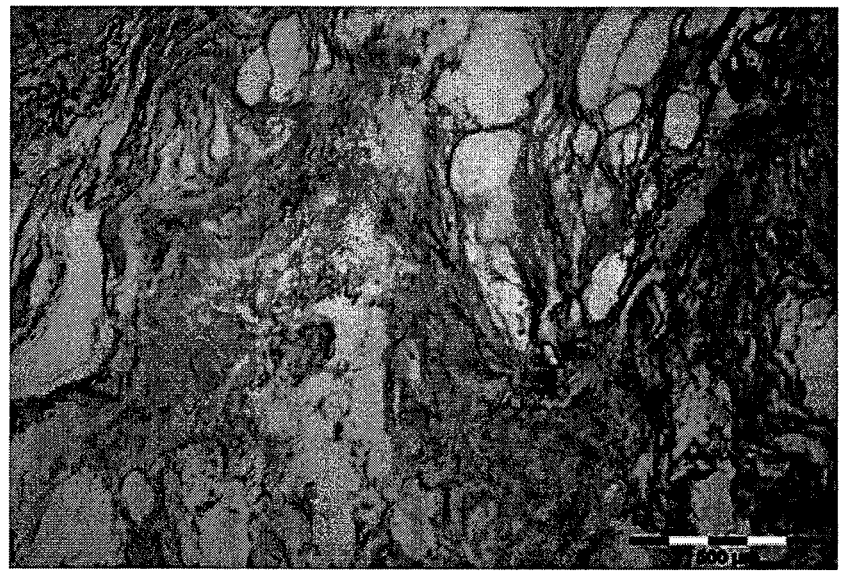
Figure 18:
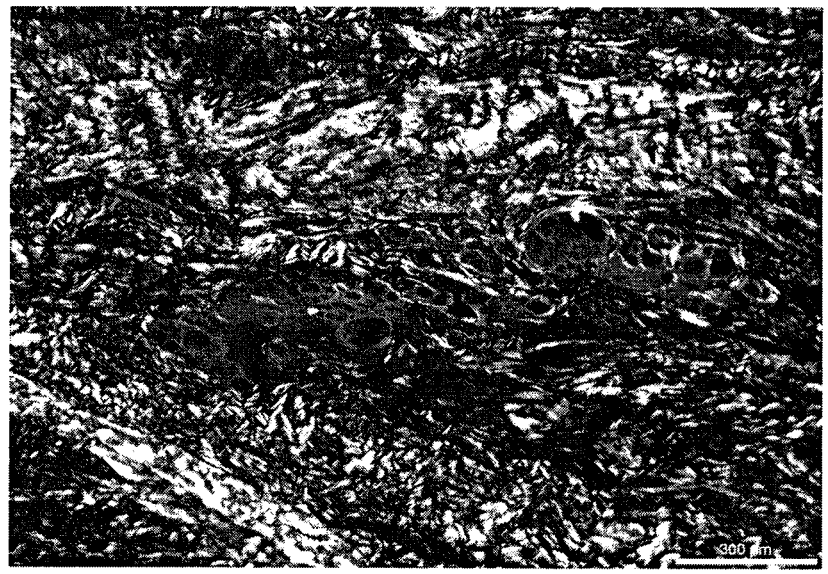

FIG. 4 shows A: MSCs labelled with a green fluorescent membrane tracker dye suspended in $1C_{10}$ prior to gelation, and cultured for 2 weeks where cells can clearly be seen throughout the gel and B: the hydrogel from A was embedded in paraffin wax, 4 µm sections mounted on slides and stained with masson trichrome (collagen stain) demonstrating the cells within the hydrogel were producing collagens;

FIG. 5 shows effects of de-swelling properties of hydrogels following incorporation of gelatine dopant in liquid precursor prior to cooling;

FIG. 6 shows MSCs labelled with a green fluorescent membrane tracker dye suspended in $1C_{10}G20$ (Table 3) prior to gelation, and cultured for 2 weeks (A), and 4 weeks (B), cells can clearly be seen throughout the gel;

FIG. 7 shows the effects on the de-swelling properties of hydrogels following incorporation of hyaluronic acid (HA) dopant in liquid precursor prior to cooling;

FIG. 8 shows A: MSCs labelled with a green fluorescent membrane tracker dye suspended in $1C_{10}HA20$ (Table 4) prior to gelation, and cultured for 2 weeks where cells can clearly be seen throughout the gel and B: the hydrogel from A was embedded in paraffin wax, 4 µm sections mounted on slides and stained with Masson trichrome (collagen stain) demonstrating the cells within the hydrogel were producing collagens;

FIG. 9 shows $1C_{10}HA20$ injected into collagenase digested bovine caudal intervertebral discs, $1C_{10}HA20$ was observed to fill the large voids and smaller fissures digested by the collagenase;

FIG. 10 shows SEM of typical electrospun doped PCCH mats at (a) 10,000× magnification and (b) 30,000× magnification with fibre sizes annotated;

FIG. 11 is a sequence of photographs illustrating the mouldable characteristics of the present hydrogel;

FIG. 12 is a plot of the effect of co-monomer composition of set/gelation temperature of a range of NIPAM-clay based PCPHs;

FIG. 13 is Dynamic Mechanical Analysis data from a range of post set PCPHs as detailed in table 5 illustrated as a plot of storage modulus versus log frequency;

FIG. 14 is Dynamic Mechanical Analysis data from a range of post set PCPHs as detailed in table 5 illustrated as a plot of tan δ versus log frequency;

FIG. 15 is a confocal fluorescence image to show the even distribution of proliferating MSCs within a set PCPH;

FIG. 16 is the viability of human MSC in $1C_{10}$ containing 13% DMAC indicating good cell viability within the gelled PCPH (hydrogel);

FIG. 17 is a white light microscopic image of a section from a bovine disc;

FIG. 18 is a white light microscopic image of a section of a bovine disc in which fissures have been filed with PCPH in the liquid phase to generate the composite hydrogel in vivo.

OPTIMISATION OF AMOUNT OF CLAY, MONOMER AND INITIATOR

Various compositions produce gels with various mechanical properties but, in general, the more solids that are included in the system the greater the mechanical properties of the gel. Additionally, variation of the type of monomer will also affect the mechanical properties of the final gel. One primary objective of the present study is to successfully synthesise a PCPH that may be maintained in the liquid phase and one that will not to form a solid hydrogel immediately on polymerisation. In order to allow the reactants to remain a low viscosity liquid after polymerisation the following has been have observed:

1. The total monomer content should preferably not exceed around 20% by weight of the overall composition.
2. The total clay content should preferably not around exceed 2% by weight of the overall composition.
3. The amount of initiator does not appear as significant as the amount of monomer and clay to affect the ability to remain liquid (for example, 0.5-4% by weight of monomer has been found to be successful to achieve the PCPH in the liquid phase).

When the total monomer content is above around 20% by weight or the clay content is above around 2% by weight, regardless of any other factors, the gel has been found to solidify (self assembles) in situ during polymerisation, which is behaviour typical of a cross-linking hydrogel and is observed in Haraguchi et al systems of the type disclosed in EP 1160286. Due inter alia to the amount of clay and monomer included in these types of existing systems, polymerisation and solidification to the resulting hydrogel occurs simultaneously.

The inventors have discerned no lower limits in the amount of monomer and clay in the CHPL composition per se, as although very weak gels will be produced from PCPH formulations with low solids content, the ability to remain liquid is not affected.

Also, degassing the solution prior to polymerisation has not been found to affect the ability to remain liquid.

Hydrogel Synthesis

EXAMPLE 1

Formation of the Polymer-Clay Precursor Hydrogel (PCPH)

N-Isopropylacrylamide (NIPAM) monomer (Sigma-Aldrich UK) was used as received. The inorganic clay, synthetic hectorite "Laponite RD", (Rockwood Ltd.: $[Mg_{5.34}Li_{0.66}Si_8O_{20}(OH)_4]Na_{0.66}$) was used as the inorganic cross-linking agent, unpurified and as received. The free-radical initiator azobisisobutnitrile (AIBN) (Sigma-Aldrich UK) was used as received.

First, the clay was weighed and dispersed in water until a transparent aqueous suspension is formed. The synthetic procedure is as follows: For example, to prepare a precursor hydrogel suspension which contains 10% solids of which 1% is clay (or $1C_{10}$), a transparent aqueous suspension consisting of water (9 g) exfoliated inorganic clay (0.1 g) (or 9.1 g of the original exfoliated suspension), AIBN (0.009 g) and NIPAM (0.9 g) was prepared (N.B. In all cases, AIBN concentration is 1% that of NIPAM). Then, polymerisation was allowed to proceed in an oil bath preset to 80° C. for a minimum of 25 minutes. The nomenclature format is as follows:

$xC_y$

Where x is the overall percentage of clay by weight, and $y$ denotes the overall percentage of "solids" (clay+NIPAM) by weight of the precursor hydrogel and subsequent gel. For example, "$1C_{20}$" indicates a 10 g sample of precursor hydrogel prepared using 8 g water, 1.9 g NIPAM, 0.1 g clay, 0.019 g AIBN. "$0.5C_{10}$" indicates a 10 g sample of precursor hydrogel prepared using 9 g water, 0.95 g NIPAM, 0.05 g clay, 0.0095 g AIBN as detailed in table 1.

TABLE 1

NIPAM/Clay Hydrogel Precursor Solution
Nomenclature—Component Percentages by Weight

| Component | $.1C_1$ | $.1C_5$ | $.1C_{10}$ | $.1C_{15}$ | $.1C_{20}$ | $.1C_{25}$ |
|---|---|---|---|---|---|---|
| PNIPAM | 0.9 | 4.9 | 9.9 | 14.9 | 19.9 | 24.9 |
| Clay | 0.1 | 0.1 | 0.1 | 0.1 | 0.1 | 0.1 |
| H20 | 99 | 95 | 90 | 85 | 80 | 75 |

| Component | $.25C_1$ | $.25C_5$ | $.25C_{10}$ | $.25C_{15}$ | $.25C_{20}$ | $.25C_{25}$ |
|---|---|---|---|---|---|---|
| PNIPAM | 0.75 | 4.75 | 9.75 | 14.75 | 19.75 | 24.75 |
| Clay | 0.25 | 0.25 | 0.25 | 0.25 | 0.25 | 0.25 |
| H20 | 99 | 95 | 90 | 85 | 80 | 75 |

| Component | $.5C_1$ | $.5C_5$ | $.5C_{10}$ | $.5C_{15}$ | $.5C_{20}$ | $.5C_{25}$ |
|---|---|---|---|---|---|---|
| PNIPAM | 0.5 | 4.5 | 9.5 | 14.5 | 19.5 | 24.5 |
| Clay | 0.5 | 0.5 | 0.5 | 0.5 | 0.5 | 0.5 |
| H20 | 99 | 95 | 90 | 85 | 80 | 75 |

| Component | | $1C_5$ | $1C_{10}$ | $1C_{15}$ | $1C_{20}$ | $1C_{25}$ |
|---|---|---|---|---|---|---|
| PNIPAM | — | 4 | 9 | 14 | 19 | 24 |
| Clay | — | 1 | 1 | 1 | 1 | 1 |
| H20 | — | 95 | 90 | 85 | 80 | 75 |

| Component | | $1.5C_5$ | $1.5C_{10}$ | $1.5C_{15}$ | $1.5C_{20}$ | $1.5C_{25}$ |
|---|---|---|---|---|---|---|
| PNIPAM | — | 3.5 | 8.5 | 13.5 | 18.5 | 23.5 |
| Clay | — | 1.5 | 1.5 | 1.5 | 1.5 | 1.5 |
| H20 | — | 95 | 90 | 85 | 80 | 75 |

| Component | | $2C_5$ | $2C_{10}$ | $2C_{15}$ | $2C_{20}$ | $2C_{25}$ |
|---|---|---|---|---|---|---|
| PNIPAM | — | 3 | 8 | 13 | 18 | 23 |
| Clay | — | 2 | 2 | 2 | 2 | 2 |
| H20 | — | 95 | 90 | 85 | 80 | 75 |

| Component | | $2.5C_5$ | $2.5C_{10}$ | $2.5C_{15}$ | $2.5C_{20}$ | $2.5C_{25}$ |
|---|---|---|---|---|---|---|
| PNIPAM | — | 2.5 | 7.5 | 12.5 | 17.5 | 22.5 |
| Clay | — | 2.5 | 2.5 | 2.5 | 2.5 | 2.5 |
| H20 | — | 95 | 90 | 85 | 80 | 75 |

| Component | | $3C_5$ | $3C_{10}$ | $3C_{15}$ | $3C_{20}$ | $3C_{25}$ |
|---|---|---|---|---|---|---|
| PNIPAM | — | 2 | 7 | 12 | 17 | 22 |
| Clay | — | 3 | 3 | 3 | 3 | 3 |
| H20 | — | 95 | 90 | 85 | 80 | 75 |

It was discovered that in the case of clay cross-linked PNIPAM initiated by heat, polymer propagation and the act of cross-linking occurred separately. After being polymerised to completion at 80° C., the precursor hydrogel is a low viscosity, opaque liquid. When the temperature of the liquid is reduced to ~35° C., it begins to solidify, subsequently forming a clear gel. The formation of this gel is permanent and the gel does not re-liquefy when the temperature is increased.

It was also discovered that the precursor hydrogel liquid remains liquid at temperatures between 37° C. and 80° C., including instances where the precursor undergoes "cycling" between these temperatures (24 h held at 37° C. followed by 24 h held at 80° C., repeated over 14 days). The cycling process does not affect the precursor's ability to spontaneously form a clear gel on cooling. The gel formulations produced successfully are highlighted in table 2.

TABLE 2

NIPAM-Clay Precursor Hydrogel Solutions

| Overall % Clay | 1 | 5 | 10 | 15 | 20 | 25 |
|---|---|---|---|---|---|---|
| 0.1 | $.1C_1$ | $.1C_5$ | $.1C_{10}$ | $.1C_{15}$ | $.1C_{20}$ | $.1C_{25}$ |
| 0.25 | $.25C_1$ | $.25C_5$ | $.25C_{10}$ | $.25C_{15}$ | $.25C_{20}$ | $.25C_{25}$ |
| 0.5 | $.5C_1$ | $.5C_5$ | $.5C_{10}$ | $.5C_{15}$ | $.5C_{20}$ | $.5C_{25}$ |
| 1 | N/A | $1C_5$ | $1C_{10}$ | $1C_{15}$ | $1C_{20}$ | $1C_{25}$ |
| 1.5 | N/A | $1.5C_5$ | $1.5C_{10}$ | $1.5C_{15}$ | $1.5C_{20}$ | $1.5C_{25}$ |
| 2 | N/A | $2C_5$ | $2C_{10}$ | $2C_{15}$ | $2C_{20}$ | $2C_{25}$ |
| 2.5 | N/A | $2.5C_5$ | $2.5C_{10}$ | $2.5C_{15}$ | $2.5C_{20}$ | $2.5C_{25}$ |
| 3 | N/A | $3C_5$ | $3C_{10}$ | $3C_{15}$ | $3C_{20}$ | $3C_{25}$ |

A number of experiments were undertaken to investigate the tolerance of living biologically active species to the nano-composite gel, both in the final gelled state and the low viscosity liquid phase.

Assessing Mesenchymal Stem Cell Viability in Presence of NIPAM Hydrogel

Fully reacted liquid precursor prepared as above was cooled to below the gelation point by pouring into a pre-prepared cavity mould to produce a cast sheet at approximately 2 mm thickness.

A 5 mm² piece of the cast gel sheet was held in growth media containing human mesenchymal stem cells (MSCs) at a concentration of 100,000 cells per ml. Cells were maintained with the gel sheet suspended within a cell culture insert at 37° C., 5% $CO_2$ for 14 days.

Figure 1:
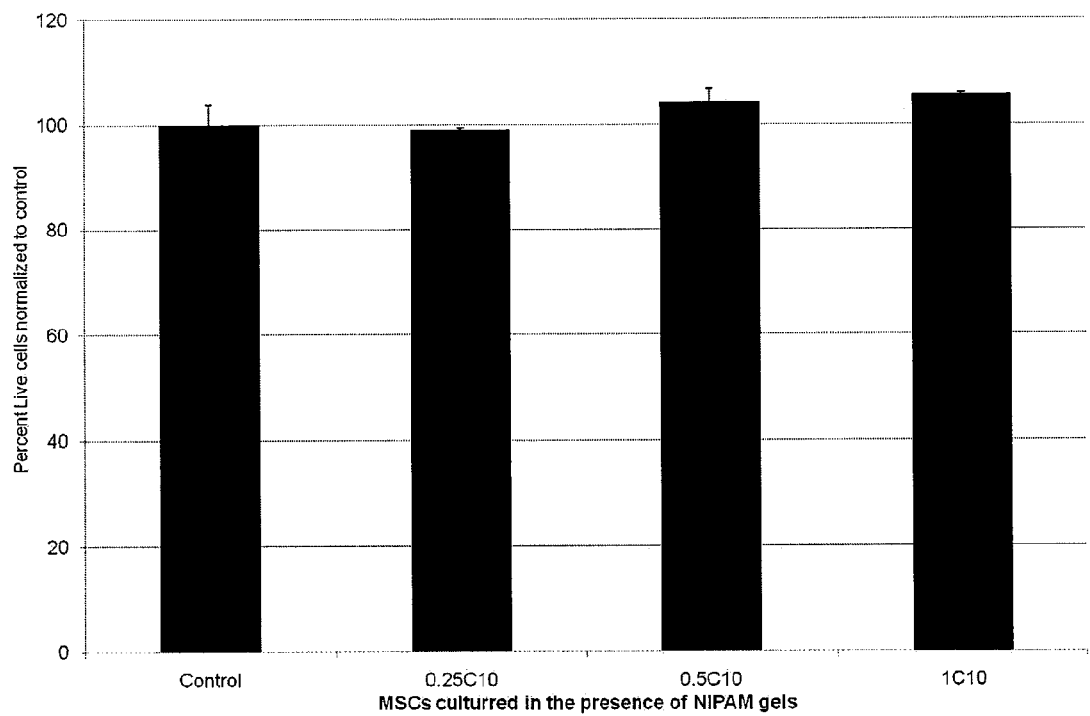
FIG. 1 shows cell viability of Human mesenchymal stem cells (MSCs) cultured in the presence of NIPAM gels for 2 weeks prior to assessment of viability.

A cell viability assay using Hoechst/propidium iodide staining and live/dead cell counts was performed in samples prepared by this method and compared to counts from controls inoculated from the same cell cultures without gel present. A number of gel formulations were tested including: $0.25C_{10}$, $0.5C_{10}$ and $1C_{10}$. Viable cell numbers were not affected by culture with any of the gel sheets as shown in FIG. 1, showing that the gel did not release any toxic substances into the culture media and thus was not cytotoxic to the MSCs.

Adherence of MSCs to Pre-Cast Hydrogels

Fully reacted liquid gel ($1C_{10}$) was cooled to below the gelation point by pouring into a pre-prepared cavity mould to produce a cast sheet at approximately 2 mm thickness.

A sample of the gel sheet approximately 5 mm² was placed into an in vitro culture plate. MSCs (pre labelled with a green fluorescence membrane dye) in growth media were inoculated onto the surface of the sheet (100,000 cells per gel sheet) and incubated at 37° C., 5% $CO_2$ for up to 6 weeks.

Figure 2:
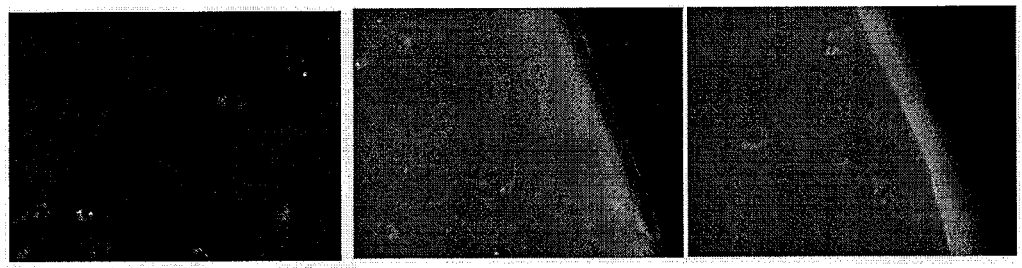
FIG. 2 shows MSC cells labelled with cell tracker dye, A: Control cells cultured on tissue culture plastic with no NIPAM, and B: Cells cultured in presence of $1C_{10}$ gel (for details of composition refer to Table 1) adhered to tissue culture plastic and, C: Cells cultured in presence of $1C_{10}$ gel adhered to $1C_{10}$ gel hydrogel layer.

MSCs adhered to the surface of the gel sheet within 24 hrs. MSCs were clearly visible on the surface of the sheet during culture as shown in FIG. 2.

Migration of MSCs Through Pre-Cast Hydrogels

Fully reacted liquid gel ($1C_{10}$) was cooled to below the gelation point by pouring into a pre-prepared mould to cast a rod of approximately 5 mm diameter by 40 mm length.

A 15 mm slice was taken from the gel rod to give a cylinder of 5 mm diameter×15 mm height. This cylinder was placed into a 12 well plate and the top, exposed surface was inoculated with 100,000 MSCs. The sample was then incubated at 37° C., 5% $CO_2$ for 14 days.

Figure 3:
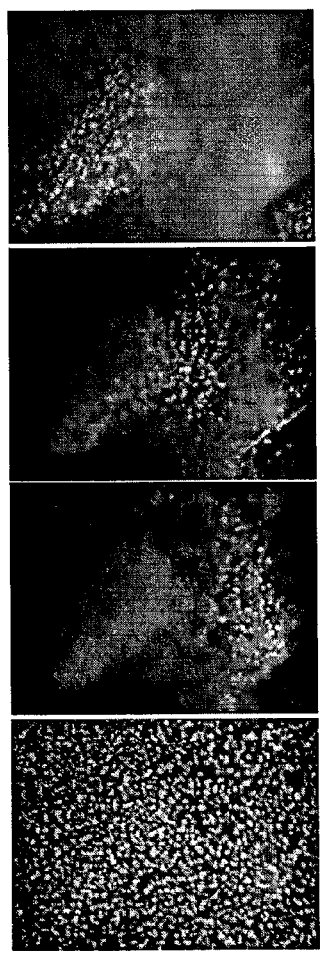
FIG. 3 shows migration of MSCs through $1C_{10}$ hydrogel during a 2 week culture, where cells can clearly be visualized throughout the hydrogel following seeding to the surface of the hydrogel.

Following incubation time, the gel cylinder was examined for the presence of living MSCs using nuclei staining with Hoescht (blue nuclei dye). Cells were clearly visible at the surface of the gel cylinder. The gel cylinder was also sectioned at intervals of 2.5 mm. Each section showed clear presence of viable cells, due to migration into and through the gel as shown in FIG. 3.

Suspension of MSCs in the Liquid PCPH Prior to Gelation

The PCPH ($1C_{10}$) was cooled to 38° C., remaining as a low viscosity liquid. One million MSCs (pre labelled with green fluorescent membrane tracker dye) per ml of liquid gel (this is similar to cell numbers observed within the centre of the intervertebral disc) were added to the liquid gel and 0.05 ml pipetted into a 96 well plate at 38° C. The plate was then cooled to 35° C. causing the liquid gel to irreversibly solidify. Growth media was added (0.2 ml) and the gel was incubated at 37° C., 5% $CO_2$ for up to 28 days.

Following incubation, MSCs were visible throughout the gel, demonstrating good viability as shown in FIG. 4a. Evidence was also seen through the use of specific histological stains for production of collagen matrix within the gel by the cells as shown in FIG. 4b.

EXAMPLE 2

Formation of Gelatine-Incorporated PCPH

The liquid phase PCPH was synthesised as per Example 1.

A gelatine solution was made by warming a 1:1 w/w mixture of gelatine granules (Fluka Analytical) and deionised water to 70° C. and stirring until smooth. A measured quantity of this solution was combined with the PCPH and carefully stirred in a heated ultrasonic bath (40 KHz at 70° C.) until a homogenous pale-yellow liquid, the gelatine-incorporated PNIPAM-clay precursor hydrogel, is formed.

The nomenclature format for these doped gels is as follows:

$xC_yQz$

Where "$xC_y$" indicates the formulation of the base precursor hydrogel suspension (see example 1), Q denotes the specific dopant used (for example, "G" for gelatine, "H" for Hyaluronic Acid), and z is the percentage of the given dopant solution of the overall solution by weight as shown in table 3. For example, $1C_{10}G10$ indicates a gelatine-incorporated PNIPAM-Clay precursor hydrogel prepared using a $1C_{10}$ basic PCPH suspension (9 g water, 0.9 g NIPAM, 0.1 g clay, 0.009 g AIBN) to which 1.111 g gelatine solution (5.555 g gelatine, 5.555 g water), is added.

Incorporation of gelatine into NIPAM-clay precursor hydrogel systems decreased the heat-induced deswelling capacity of the resulting nanocomposite gels (measured optically after equilibration at the given temperatures for 24 h) as shown in FIG. 5 together with affecting gelation temperature. Fully reacted liquid precursor ($1C_{10}G20$) was cooled to 38° C., remaining as a low viscosity liquid. One million MSCs (pre labelled with green fluorescent membrane tracker dye) per ml of liquid gel (this is similar to cell numbers observed within the centre of the intervertebral disc) were added to the liquid gel and 0.05 ml pipetted into a 96 well plate at 38° C. The plate was then cooled to 35° C. causing the liquid gel to irreversibly solidify. Growth media was added (0.2 ml) and the gel was incubated at 37° C., 5% $CO_2$ for up to 28 days. Following incubation, MSCs were visible through the gel, demonstrating good viability as shown in FIG. 6.

EXAMPLE 3

Formation of the Hyaluronic Acid-Incorporated PCPH

The PCPH liquid was synthesised as per Example 1. A Hyaluronic Acid (HA) solution was made by firstly preparing a 50:1 w/w mixture of crude HA from bovine vitreous humour (Lyophilized, Sigma) and deionised water. The mixture was refrigerated for 48 hours, during which time it was removed and stirred vigorously every 12 hours. A measured quantity of this solution, which now was a very viscous homogeneous liquid, was then combined with the PCPH and carefully stirred in a heated ultrasonic bath (40 KHz at 40° C.) until a homogenous milky liquid, the HA-incorporated PNIPAM-clay precursor hydrogel, was formed.

The nomenclature format for these dopant gels is as follows:

$xC_yQz$

Where "$xC_y$" indicates the formulation of the base PCPH (see example 1), Q denotes the specific dopant used ("H" for Hyaluronic Acid), and z is the percentage of the given dopant solution of the overall solution by weight a shown in table 4. For example, $1C_{10}H10$ indicates a hyaluronic acid-incorporated PNIPAM-Clay precursor hydrogel prepared using a $1C_{10}$ basic PCPH (9 g water, 0.9 g NIPAM, 0.1 g clay, 0.009 g AIBN) to which 1 g hyaluronic acid solution (0.02 g hyaluronic acid, 0.98 g water), is added.

TABLE 3

Gelatine-NIPAM-Clay Precursor Hydrogel Nomenclature—Component Percentages by Weight

| Component | $10C_{10}$ G5 | $10C_{10}G10$ | $10C_{10}G15$ | $10C_{10}G20$ | $10C_{10}G25$ | $10C_{10}G50$ | $10C_{10}$ G75 |
|---|---|---|---|---|---|---|---|
| PNIPAM | 8.55 | 8.1 | 7.65 | 7.2 | 6.75 | 4.5 | 2.25 |
| Clay | 0.95 | 0.9 | 0.85 | 0.8 | 0.75 | 0.5 | 0.25 |
| H20 | 88 | 86 | 84 | 82 | 80 | 70 | 60 |
| Gelatine | 2.5 | 5 | 7.5 | 10 | 12.5 | 25 | 37.5 |

TABLE 4

| | Hyaluronic Acid-NIPAM-Clay Precursor Hydrogel Nomenclature—Component Percentages by Weight | | | | | | |
|---|---|---|---|---|---|---|---|
| Component | $10C_{10}H5$ | $10C_{10}H10$ | $10C_{10}H15$ | $10C_{10}H20$ | $10C_{10}H25$ | $10C_{10}H50$ | $10C_{10}H75$ |
| PNIPAM | 8.55 | 8.1 | 7.65 | 7.2 | 6.75 | 4.5 | 2.25 |
| Clay | 0.95 | 0.9 | 0.85 | 0.8 | 0.75 | 0.5 | 0.25 |
| H20 | 90.4 | 90.8 | 91.2 | 91.6 | 92 | 94 | 96 |
| Hyaluronic Acid | 0.1 | 0.2 | 0.3 | 0.4 | 0.5 | 1 | 1.5 |

In a similar manner to incorporation of gelatine to NIPAM-Clay precursor hydrogel, incorporation of hyaularonic acid into the precursor hydrogel also affected deswelling capacity following gelation as shown in FIG. 7. Additionally HA incorporated hydrogels appeared more adhesive to plastic culture plates. The HA-incorporated PNIPAM-Clay precursor hydrogel was cooled to 38° C., remaining as a low viscosity liquid. One million MSCs (pre labelled with green fluorescent membrane tracker dye) per ml of PCPH (this is similar to cell numbers observed within the centre of the intervertebral disc) were added to the PCPH and 0.05 ml pipetted into a 96 well plate at 38° C. The plate was then cooled to 35° C. causing the PCPH to irreversibly solidify. Growth media was added (0.2 ml) and the gel was incubated at 37° C., 5% $CO_2$ for up to 28 days. Following incubation, MSCs were visible through the gel, demonstrating good viability as shown in FIG. 8. It was also observed that the HA doped gel appears to support more cell growth.

EXAMPLE 4

Injectability of the PCPH

PCPH liquids were prepared as in Examples 1, 2 and 3. The PCPHs were held at 40° C. in liquid, injectable form. A bovine disc was prepared via injection of 0.1 ml 1 mg/ml collagenase type II for 24 hrs at 37° C., with damage induced to simulate degeneration of the nucleus pulposus (NP) and provide cavities in NP. The disc was held at 37° C., and 0.1-0.2 ml liquid gel was injected through the annulus fibrosus (outer intervertebral disc) into the NP using a 21 gauge needle. Tissues were allowed to cool to 35° C. for 10 minutes to enable solidification of the PCPH in the disc, and then maintained at 37° C. for 24 hrs.

The discs were excised from the motion segments, fixed in formalin, embedded in paraffin wax and sectioned for examination, where it was observed that the gel filled the cavities in the disc and that gel was well adhered to the internal surfaces. The gel was also observed to have filled the injection channel formed through the healthy tissues as shown in FIG. 9.

EXAMPLE 5

Electro-Spinning

PCPH liquids were prepared as in Example 2 and to this, 1,1,1,3,3,3-Hexafluoro-2-propanol (HFP) was added to give a PCPH to HFP ratio of 10:1. Electrospinning was performed by using a plastic syringe containing the HFP/PCPH mixture attached to a digitally controlled syringe pump. The transfer line, the syringe and the needle were all heated using an insulated thermal jacket set at 70° C. The needle was vertically oriented towards the collector and the tip-to-collector distance was set at 14 cm. The power voltage was fixed at 12 kV and the volumetric flow rate was set at 0.20 mL/h. FIG. 10 shows a typical SEM image of electrospun mats manufactured using this process.

EXAMPLE 6

Moulding

PCPH liquids were prepared as in Examples 1, 2, 3 and 4. Generation of PCPH of a predetermined shape was achieved by the pouring of the hot liquid PCPH into a suitable mould and allowing it to cool. The photographs of FIG. 11 show the facile formation of potentially intricate shapes and in particular (1) the free flowing low viscosity liquid, (2) the facile pipetting from stock, (3) the complete filling of the mould, (4) the opaque polymer PCPH, (5) the optically transparent composite hydrogel formed upon cooling and, (6) the composite hydrogel being easily removed upon setting and retaining its predetermined shape.

EXAMPLE 7

Combinations of Monomer and their Effect on Set Temperature, Mechanical Property and Cell Viability The setting temperature of the PCPH and the mechanical properties of the final post-set gel can be tailored by the use of a co-monomer in the starting reaction mixture. The effect on the set temperature of co-monomers, namely dimethyl acrylate (DMA, more hydrophilic than NIPAM) and glycidyl methacrylate (GMA, more hydrophobic than NIPAM) were investigated. It was anticipated that the addition of DMA would elevate the set temperature in a pseudo-linear fashion, whilst conversely the incorporation of GMA would suppress the set temperature.

FIG. 12 shows the effect of co-monomer fraction on the measured set temperature of a number of PCPH formulations. It should be noted that at high GMA fractions (>50%), the PCPH remained in liquid form even after being chilled in a refrigerator with a measured temperature of 4° C. As predicted the incorporation of DMA as a co-monomer leads to an increase in the set temperature and the incorporation of GMA as a co-monomer leads to a decrease in the set temperature. Accordingly, it has been observed that the degree of change can be controlled by the relative composition of the co-monomers.

FIGS. 13 and 14 show the results of the dynamic mechanical analysis of a series of post set formulations incorporating various amounts of water soluble additive (gelatine and hyaluronic acid) and co-monomer (GMA) (Table 5) the pseudo-linear increase in storage modulus as a function of frequency is indicative of a visco-elastic material. From this data it is clear that the incorporation of water soluble additives into the PCPH has a significantly more reduced impact upon the mechanical properties than incorporating an additional co-monomer, in this instance DMA. But it is also clear that by careful selection of clay content, water content, co-monomer content and water soluble additive content it is possible to tune particular mechanical properties into the resulting polymerised hydrogel.

TABLE 5

| Nomenclature | Nominal sample composition |
|---|---|
| 1C$_{10}$ | 1% Clay, 9% NIPAM, 90% water |
| 1C$_{10}$G10 | 0.9% Clay, 8.1% NIPAM, 5% gelatine, 86% water |
| 1C$_{10}$G20 | 0.8% Clay, 7.2% NIPAM, 10% gelatine, 82% water |
| 1C$_{10}$H10 | 0.9% Clay, 8.1% NIPAM, 0.2% hyaluronic acid, 90.8% water |
| 1C$_{10}$H20 | 0.8% Clay, 7.2% NIPAM, 0.4% hyaluronic acid, 91.6% water |
| 1C$_{10}$DMA13 | 1% Clay, 8.3% NIPAM, 0.7% DMA, 89% water |

EXAMPLE 8

Illustrations of the Homogenous Distribution of Cells within the Hydrogel

MSCs labelled with a green fluorescent dye were suspended in cell culture media and mixed at 39° C. with PCPH. The suspension was allowed to set and incubated at 37° C. for up to 7 days. Sections were taken from the set PCPH/MSC mixture which clearly show that the MSCs are evenly distributed and proliferating within the matrix (FIG. 15) within this timeframe. Cell viability data (FIG. 16) confirm that there is no negative impact on the ability of the cells to survive in the hydrogel matrix.

EXAMPLE 9

Effectiveness of the Solution to Fill Small Cavities

To confirm the effectiveness of the PCPH to fill voids in soft tissue, samples of bovine caudal disc were injected with collagenase (100 μl, 2 mg/ml, 1 hr) to mimic mild degeneration. The collagenase effectively digests all collagens within the IVD and the result is tissue with holes and fissures that are visible using white light microscopy (FIG. 17).

Using a 21 gauge needle, 500 μl of 1C$_{10}$ containing a few drops of blue food dye was injected into a bovine caudal disc treated with collagenase and incubated for 24 hours at 37° C. The IVD was removed and sections taken from the NP region of the excised tissue. FIG. 18 confirms that the set PCPH (hydrogel) has successfully and completely filled the holes generated by the collagenase.

The invention claimed is:

1. A method of preparing a non-chemically cross-linked composite hydrogel comprising:
    preparing an aqueous suspension containing (i) dispersed clay particles, (ii) a water soluble monomer and (iii) a radical initiator capable of free radical disassociation to form a composite hydrogel precursor liquid (CHPL);
    dissociating the radial initiator to provide free radical polymerisation of the monomer at a temperature above a gelation temperature of a resulting aqueous polymer-clay precursor hydrogel (PCPH);
    maintaining the PCPH in a fluid phase above the gelation temperature; and reducing the temperature of the PCPH below its gelation temperature to provide a composite hydrogel.

2. The method as claimed in claim 1 wherein the water soluble monomer comprises an acrylamide.

3. The method as claimed in claim 2 wherein the acrylamide monomer comprises a compound of formula I:

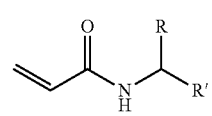

(I)

where R and R' are both alkyl, phenyl, or alkyl-phenyl.

4. The method as claimed in claim 1 wherein the monomer comprises any one or a combination of the following:
    Acrylic acids;
    Acid anhydrides;
    Acrylates;
    Sulfonic acids;
    Vinyl sulfonates;
    Pyrolidones;
    N-isopropylacrylamide (NIPAM);
    N,N-dimethylacrylamide;
    Glycerol monomethacrylate;
    Hydroxyl ethyl Methacrylate;
    Polyethyleneglycomethacrylate;
    Vinyl pyrolidone; and
    Styrene sulphonic acid.

5. The method as claimed in claim 1 wherein the water soluble monomer is an acrylate compound of formula II

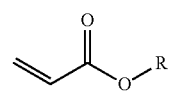

(II)

where R is a hydrophilic, acrylate or amide group.

6. The method as claimed in claim 1 wherein the PCPH comprises any one or a combination of the following set of:
    a polymer formed from a single monomer;
    a polymer formed from at least two different monomers; and
    a block copolymer.

7. The method as claimed in claim 2 wherein the gelation temperature of the PCPH is in the range 30° C. to 40° C.; and
    wherein the step of disassociating the radial initiator comprises heating the CHPL above 40° C.

8. The method as claimed in claim 1 further comprising heating the CHPL to a temperature in the range 40° C. to 100° C.

9. The method as claimed in claim 1 wherein the initiator comprises an azonitrile.

10. The method as claimed in claim 1 wherein the clay comprises a swellable clay, capable of ion exchange.

11. The method as claimed in claim 1 wherein the clay comprises any one or a combination of the following set of:
    montmorillonite;
    hectorite;
    saponite;
    vermiculite;
    mica;
    bentonite; and
    a fibrous clay.

12. The method as claimed in claim 1 further comprising introducing into the PCPH at least one or a combination of biologically active species selected from the list of:
- mammalian cells;
- an antimicrobial;
- an antibody;
- a bacteria;
- a protein;
- a pharmaceutical; and
- a peptide.

13. The method as claimed in claim 1 further comprising introducing into the CHPL and/or the PCPH, a compound comprising any one or a combination of the following set of:
- a water soluble polymer;
- hyaluronic acid;
- hydrophilic gels;
- polyethylene glycol, polypropylene glycol and mixtures thereof;
- cellulose ethers;
- chitosan;
- alginates;
- proteoglycans;
- natural starches;
- collagen;
- gelatine; and
- hydroxyapatite.

14. The method as claimed in claim 1 further comprising introducing into the CHPL and/or PCPH comprising any one or a combination of the following process additives:
- a thickener;
- a rheology modifier;
- a surfactant;
- a pigment or dye; and
- a radio opaque material.

15. The method as claimed in claim 1 wherein the polymer resultant from the polymerisation of the monomer is cross-linked by the clay particles.

16. The method as claimed in claim 1 wherein chains of the polymer resultant from polymerisation of the monomer are anchored at one or both ends to a surface of the clay particles.

17. The method as claimed in claim 1 wherein the clay particles act as cross-linkages between polymer chains resultant from polymerisation of the monomer such that the clay particles and the polymer resultant from polymerisation of the monomer are interconnected.

18. A method of creating a non-chemically cross-linked composite hydrogel in an animal or human in vivo comprising:
- injecting into a human or animal an aqueous polymer-clay precursor hydrogel (PCPH) containing a polymer and a clay, the PCPH maintained above its gelation temperature before and during the step of injecting; and
- allowing the temperature of the PCPH to decrease below the gelation temperature in vivo to form a composite hydrogel.

19. The method as claimed in claim 18 comprising injecting the aqueous PCPH into a spinal disc of the animal or human.

20. The method as claimed in claim 18 comprising injecting the aqueous PCPH into a region of soft or hard tissue of the animal or human.

21. The method as claimed in claim 18 further comprising doping the aqueous PCPH with a biologically active species prior to the step of injecting.

22. The method as claimed in claim 21 wherein the bioactive species comprises any one or a combination of the following set of:
- mammalian cells;
- an antimicrobial;
- an antibody;
- a bacteria;
- a protein;
- a pharmaceutical; and
- a peptide.

23. The method as claimed in claim 22 further comprising doping the aqueous PCPH with a compound comprising any one or a combination of the following set of:
- a water soluble polymer;
- hyaluronic acid;
- hydrophilic gels;
- polyethylene glycol, polypropylene glycol and mixtures thereof;
- cellulose ethers;
- chitosan;
- alginates;
- proteoglycans;
- natural starches;
- collagen;
- gelatine; and
- hydroxyapatite.

* * * * *